United States Patent [19]

Fumihiko et al.

[11] Patent Number: 5,565,611
[45] Date of Patent: Oct. 15, 1996

[54] PROCESS FOR PREPARING ACID ADDITION SALT OF Z-ISOMER OF TRIPHENYLETHYLENE COMPOUND

[75] Inventors: Shinozaki Fumihiko, Kodama-gun; Nagasawa Hiroshi, Honjo; Maruhashi Kazuo, Kawagoe, all of Japan

[73] Assignee: Taiho Pharmaceutical Co., Ltd., Tokyo, Japan

[21] Appl. No.: 446,736

[22] Filed: Jun. 6, 1995

[30] Foreign Application Priority Data

Oct. 25, 1993 [JP] Japan ................................ 5-266620

[51] Int. Cl.$^6$ .................................................. C07C 213/10
[52] U.S. Cl. .................... 564/324; 544/174; 544/396; 546/236; 548/575; 558/414; 560/58; 560/101; 560/142; 560/133
[58] Field of Search .............................................. 564/324

[56] References Cited

U.S. PATENT DOCUMENTS 4,960,937 10/1990 Woschina et al. ...................... 564/324
4,973,755 11/1990 Grafe et al. ............................. 564/324

FOREIGN PATENT DOCUMENTS 59-225151 12/1984 Japan .
0313799 9/1988 Japan .

OTHER PUBLICATIONS

J. Synth. Org. Chem., 1987, pp. 816–817, Mohammed I. Al–Hassan, A Single–Step Synthesis of Tamoxifen Using Palladium–Catalyzed Cross Coupling.
Synth. Commun., 1987, pp. 1247–1251, Mohammed I. Al–Hassan, Synthesis of cis–and trans–tamoxifen, punlished on 1987, U.S.
J. Chem. Soc. Perkin Trans. II 1988, "The Role of the 2–Methyl Substituent in Governing Stereoselective Formation of the E Isomer in the Synthesis of 4–Hydroxy–2–methyltamoxifen (1–{4–[2–(Di–methylamino)ethoxy]phenyl}–1–(4–hydroxy–2–methylphenyl)–2phenylbut– 1–ene)", Raymond McCague et al, pp. 1201–1208.

Chemical Abstract, vo. 118, 1993, p. 842, Abstract No. 118:254522g, "Preparation of tamoxifen citrate without separation of the geometric isomers".

Primary Examiner—Richard L. Raymond
Attorney, Agent, or Firm—Nikaido, Marmelstein, Murray & Oram LLP

[57] ABSTRACT

The present invention provides a process for preparing an acid addition salt of the Z-isomer of a compound of the formula

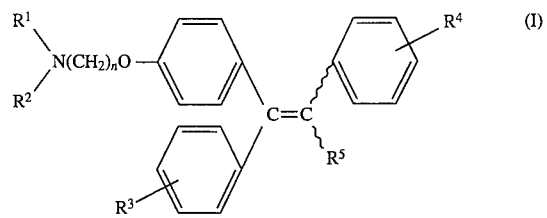

wherein $R^1$ and $R^2$ represent a lower alkyl group, or taken together with the nitrogen atom to which they are attached, form a nitrogen-containing heterocyclic group optionally containing other hetero atom or atoms; $R^3$ and $R^4$ represent H, a lower alkyl group, OH, a lower alkoxy group, a lower alkylcarbonyloxy group, an arylcarbonyloxy group optionally substituted with 1–2 substituents selected from lower alkyl, lower alkoxy, halo and CN on the benzene ring, a benzylcarbonyloxy group, a mono- or di(lower alkyl)aminocarbonyloxy group or a mono- or di(aryl)aminocarbonyloxy group; $R^5$ represents a lower alkyl group or halo; and n represents 1–6, characterized in that the E-isomer of the compound of the formula (I) or its acid addition salt, singly or in admixture with the Z-isomer or its acid addition salt, is heated in an organic solvent containing hydrobromic acid.

15 Claims, No Drawings

PROCESS FOR PREPARING ACID ADDITION SALT OF Z-ISOMER OF TRIPHENYLETHYLENE COMPOUND

This application is a 371 of PCT/JP94/01782, filed Oct. 25, 1994.

TECHNICAL FIELD

The present invention relates to a process for preparing acid addition salts of Z-isomers of triphenylethylene compounds such as non-steroidal antiestrogenic agents, typically tamoxifen, which are useful for treating hormone dependent tumors, and 1-(4-hydroxyphenyl)-2-(4-isopropylphenyl)-1-[4-(2-N,N-dimethylamino)ethoxy]phenyl-1-butene which is known as an important intermediate of said non-steroidal antiestrogenic agents, by converting the E-isomers.

BACKGROUND ART

Tamoxifen, one of the triphenylethylene compounds, is the Z-isomer of 1,2-diphenyl-1-[4-(2-N,N-dimethylamino)ethoxy]phenyl-1-butene as shown by the following formula.

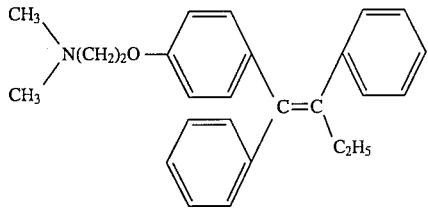

Concerning the synthesis of tamoxifen or the corresponding E-isomer, many methods have been reported (e.g., Journal of the Chemical Society Perkin Transactions I, (3), 475 (1986) and Synthetic Communications, 17 (10), 1247 (1987)). In these well-known methods, however, the corresponding E-isomer and Z-isomer are formed as a mixture. Of the two isomers, only the Z-isomer has the desired biological activities and therefore the Z-isomer must be separated by fractional crystallization, chromatography or the like.

In the synthesis of 1-(4-hydroxyphenyl)-2-(4-isopropylphenyl)-1-[4-(2-N,N-dimethylamino)ethoxy]phenyl-1-butene as well, a mixture of the E-isomer and the Z-isomer is formed. However, of the E-isomer and the Z-isomer of the end products which are derived from these compounds, only the Z-isomer has the desired biological activities. Therefore, Z-isomer needs to be separated from the mixture by means of fractional crystallization, chromatography or the like, as in the preparation of tamoxifen. Another problem is a high cost of producing the Z-isomer because only a limited amount of the Z-isomer is collected.

Also a method is reported wherein a mixture of a hydrochloric acid salt of tamoxifen and a hydrochloric acid salt of its E-isomer is heated in a concentrated hydrochloric acid for many hours to thereby convert the hydrochloric acid salt of the E-isomer to a hydrochloric acid salt of tamoxifen (Japanese Examined Patent Publication (Kokoku) No. 75224/1992). However, when the inventors of the present invention employed this technique in an attempt to convert 1-(4-hydroxyphenyl)-2-(4-isopropylphenyl)-1-[4-(2-N,N-dimethylamino)ethoxy]phenyl-1-butene or the like under the same condition, the application of this technique proved to be unsuccessful because the rate of decomposition was faster than the rate of conversion. This technique further has a problem of increased cost because safety should be assured against a large excess amount, i.e., 20 equivalents or more, of the strong acid used with heating and the conversion takes a long period of time of at least 8 hours.

DISCLOSURE OF THE INVENTION

The inventors of the present invention carried out intensive research in order to solve the above-mentioned problems, and found that, by heating the E-isomer of a triphenylethylene compound, such as 1-(4-hydroxyphenyl)-2-(4-isopropylphenyl)-1-[4-(2-N,N-dimethylamino)ethoxy]phenyl-1-butene, or an acid addition salt thereof singly or in admixture with its Z-isomer or an acid addition salt thereof in an organic solvent which contains hydrobromic acid, an acid addition salt of the Z-isomer can be produced in high yields. The present invention has been accomplished based on this finding.

Thus, the present invention provides a process for preparing an acid addition salt of the Z-isomer of a triphenylethylene compound of the formula

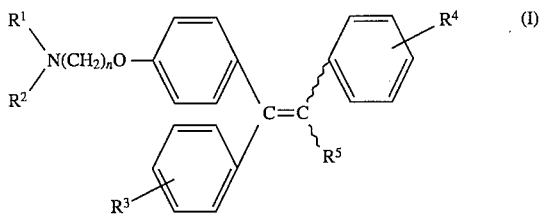

wherein $R^1$ and $R^2$ are the same or different and they each represent a lower alkyl group, or $R^1$ and $R^2$, taken together with the nitrogen atom to which they are attached, may form a nitrogen-containing heterocyclic group which optionally contains other hetero atom or atoms; $R^3$ and $R^4$ are the same or different and they each represent a hydrogen atom, a lower alkyl group, a hydroxyl group, a lower alkoxy group, a lower alkylcarbonyloxy group, an arylcarbonyloxy group optionally substituted with one or two substituents selected from the group consisting of a lower alkyl group, a lower alkoxy group, a halogen atom and a cyano group on the benzene ring, a benzylcarbonyloxy group, a mono- or di(lower alkyl)aminocarbonyloxy group or a mono- or di(aryl)aminocarbonyloxy group; $R^5$ represents a lower alkyl group or a halogen atom; and n represents an integer of 1–6, the process being characterized in that the E-isomer of the triphenylethylene compound of the formula (I) or an acid addition salt thereof is heated in an organic solvent which contains hydrobromic acid.

The present invention also provides a process for preparing an acid addition salt of the Z-isomer of the compound of the formula (I), characterized in that the E-isomer of the compound of the formula (I) or an acid addition salt thereof, as admixed with the Z-isomer of the compound of the formula (I) or an acid addition salt thereof, is heated in an organic solvent containing hydrobromic acid.

In the formula (I), the lower alkyl groups represented by $R^1$ through $R^5$ include, for example, straight- or branched-chain alkyl groups having 1 to 6, preferably 1 to 4, carbon atoms, such as methyl, ethyl, n-propyl, isopropyl, n-butyl, isobutyl, sec-butyl, tertbutyl, pentyl and hexyl.

The nitrogen-containing heterocyclic group which $R^1$ and $R^2$ form together with the nitrogen atom to which they are attached includes, for example, a five- or six-membered nitrogen-containing heterocyclic group which contains 1 or 2 nitrogen atoms and which optionally contains 1 or 2 other hetero atoms such as oxygen atom. Preferable examples thereof are 1-piperidyl group, 1-piperazinyl group, 4-morpholinyl group and 1-pyrrolidinyl group.

The lower alkoxy groups represented by $R^3$ and $R^4$ include, for example, straight- or branched-chain alkoxy groups having 1 to 6 carbon atoms, such as methoxy, ethoxy, n-propoxy, isopropoxy, n-butoxy, isobutoxy, sec-butoxy, tert-butoxy, n-pentyloxy, isopentyloxy and n-hexyloxy.

The lower alkylcarbonyloxy group represented by $R^3$ and $R^4$ means a carbonyloxy group to which the above-mentioned lower alkyl group is attached.

The mono- or di(lower alkyl)aminocarbonyloxy group represented by $R^3$ and $R^4$ means an aminocarbonyloxy group wherein one or two of the hydrogen atoms of the amino group are substituted with the above-mentioned lower alkyl group.

The halogen atom represented by $R^5$ includes fluorine atom, chlorine atom, bromine atom and iodine atom.

In the optionally substituted arylcarbonyloxy group represented by $R^3$ and $R^4$, the lower alkyl group lower alkoxy group and halogen atom which may be substituted on the benzene ring each mean the above-mentioned groups.

The arylcarbonyloxy group represented by $R^3$ and $R^4$ which is optionally substituted with one or two substituents selected from the group consisting of a lower alkyl group, a lower alkoxy group, a halogen atom and a cyano group on the benzene ring includes phenylcarbonyloxy groups which may have one or two of the above-mentioned substituents on the benzene ring. A typical example thereof is a phenylcarbonyloxy group wherein the substituent or substituents may be 2-methyl, 4-methyl, 2-ethyl, 4-methoxy, 2-chloro, 3-chloro, 4-chloro, 2,6-dichloro, 4-bromo or 4-cyano.

The mono- or di(aryl)aminocarbonyloxy group means an aminocarbonyloxy group wherein one or two of the hydrogen atoms of the amino group are substituted by an aryl group such as a phenyl group. Typical examples thereof are phenylaminocarbonyloxy group and the like.

In the formula (I), n represents an integer of 1–6, preferably an integer of 1–3.

Of the compounds of the formula (I), preferable are those of the formula (I) wherein $R^1$ and $R^2$ are the same or different and each represents a lower alkyl group, $R^3$ and $R^4$ are the same or different and each represents a hydrogen atom, a lower alkyl group or a hydroxyl group, $R^5$ represents a lower alkyl group, and n represents an integer of 1–6, preferably an integer of 1–3.

More preferable compounds are those of the formula (I) wherein $R^1$ and $R^2$ each represents methyl group, $R^3$ represents 4-hydroxyl group, $R^4$ represents 4-isopropyl group, $R^5$ represents ethyl group, and n is 2.

The starting material, i.e., the E-isomer and Z-isomer of the triphenylethylene compound of the formula (I) are known or may be readily obtained by a conventional synthesis method, for example, by carrying out the reactions similar to those employed for preparing tamoxifen, as described in Journal of the Chemical Society Perkin Transactions I, (3), 475 (1986) and Synthetic Communications, 17 (10), 1247 (1987), and effecting isolation by means of chromatography or the like.

As the acid addition salt of the E-isomer of the triphenylethylene compound of the formula (I), salts prepared by reaction with a pharmaceutically acceptable acid by a conventional method are preferable. Typical examples are salts with an inorganic acid such as hydrochloric acid, hydrobromic acid, sulfuric acid or phosphoric acid, and an organic acid such as acetic acid, oxalic acid, maleic acid, fumaric acid, malic acid, tartaric acid, citric acid, benzoic acid, p-toluenesulfonic acid or ethanesulfonic acid.

Preferable acid addition salts include, for example, hydrochloric acid salt and hydrobromic acid salt.

Although the concentration of hydrobromic acid used in the invention is preferably at least about 30 wt. %, particularly about 47 wt. %, the concentration is not specifically limited, and it is suitable that hydrobromic acid be used, as dissolved in an organic solvent, in an amount of 0.05–1.5 moles, calculated as hydrogen bromide, per mole of the E-isomer of the compound of the formula (I) or its acid addition salt.

The organic solvent to be used in the reaction is not particularly limited insofar as it can dissolve the starting materials and hydrobromic acid and does not participate in the conversion. Typical examples thereof include aromatic hydrocarbons such as benzene, toluene and xylene, halogenated hydrocarbons such as dichloromethane and chloroform, ethers such as diethyl ether, tetrahydrofuran, dioxane and anisole, esters such as methyl acetate and ethyl acetate, ketones such as acetone and methyl ethyl ketone, and aprotic polar solvents such as acetonitrile, dimethylsulfoxide, N,N-dimethylformamide and N,N-dimethylacetamide. These solvents can be used singly or at least two of them may be used in admixture. Of these solvents, those which hardly tend to dissolve the desired acid addition salt of the Z-isomer at about room temperature are preferable. More preferably, a solvent mixture of ethyl acetate and toluene, or dichloromethane is used.

The organic solvent is preferably used in an amount of about 1–3 liters, most preferably about 2 liters, per mole of the starting material, i.e., the E-isomer of the triphenylethylene compound or its acid addition salt.

When the E-isomer is used in the form of a free base, hydrobromic acid is preferably used in an amount slightly exceeding the equimolar amount, particularly about 1.1–1.5 moles, most preferably about 1.2 moles, calculated as hydrogen bromide, per mole of the E-isomer free base. When the E-isomer is used in the form of an acid addition salt, a small amount of hydrobromic acid is sufficient, and generally the hydrobromic acid is preferably used in an amount of 0.05 to 0.5 mole, most preferably 0.2 mole, calculated as hydrogen bromide, per mole of the E-isomer acid addition salt.

The starting E-isomer of the triphenylethylene compound of the formula (I), when added in the form of free base to the organic solvent containing hydrobromic acid, is converted to a hydrobromic acid salt of the Z-isomer in the process of the conversion. When a hydrobromic acid salt of the E-isomer of the compound of the formula (I) is used as the starting material, the desired Z-isomer hydrobromic acid salt can be produced according to the present invention. The E-isomer of the compound of the formula (I), when used in the form of a salt other than the hydrobromic acid salt (e.g. salt with the above-mentioned organic or inorganic acid), can be converted to the corresponding Z-isomer acid addition salt with said acid addition salt retained. However, the rate of conversion varies depending on the kind of the acid addition salt and the kind of the organic solvent, and therefore it is recommendable that said acid addition salt of the E-isomer be changed into a free base in advance by a conventional method and then added to the organic solvent containing hydrobromic acid. Where the conversion reaction is carried out without previous change into a free base, the conversion can be accelerated by increasing the amount of hydrobromic acid or elevating the heating temperature when the conversion rate is slow.

According to the present invention, the E-isomer of the triphenylethylene compound of the formula (I) or its acid addition salt, as mixed with the corresponding Z-isomer or its acid addition salt, can also be converted to an acid addition salt of the Z-isomer under substantially the same conditions as above. In such a case, the ratio of the E-isomer or its acid addition salt to the Z-isomer or its acid addition salt can vary freely, but generally the amount of the Z-isomer or its acid addition salt in the mixture is preferably about 5–40 wt. %, in particular about 15–40 wt. %, more preferably about 25–40 wt. %, based on the total amount of the E-isomer or its acid addition salt and the Z-isomer or its acid addition salt.

The Z-isomer of the compound of the formula (I) or an acid addition salt thereof to be admixed is also known or can be prepared by a known method. Furthermore, in the conventionally known methods of preparing the compound of the formula (I), a mixture of the E-isomer (or its acid addition salt) and the Z-isomer (or its acid addition salt) is obtained, and therefore such mixture can also be used as the starting material of the process of the present invention. As the acid addition salts of the Z-isomer, any salt with the same acid as in the case of the acid addition salts of the E-isomer mentioned hereinbefore can be used.

Preferable acid addition salts of the Z-isomer are hydrochloric acid salt and hydrobromic acid salt.

When the starting material in the form of such a mixture is heated according to the present invention in an organic solvent containing hydrobromic acid, the E-isomer free base in the starting material is converted to a hydrobromic acid salt of the Z-isomer as described above, and the Z-isomer free base in the starting material is converted to a hydrobromic acid salt of the Z-isomer as such. When an acid addition salt of the E-isomer and/or an acid addition salt of the Z-isomer is/are used as the starting material, too, the corresponding acid addition salt or salts of the Z-isomer can be obtained. In view of this, when acid addition salts of the E-isomer and of the Z-isomer are used as the starting material, it is preferable that the same kind of acid addition salt be used. The rate of conversion varies depending on the kind of the acid addition salt and the kind of the organic solvent, and therefore it is recommendable that the E-isomer acid addition salt and the Z-isomer acid addition salt in the starting mixture be changed into free bases in advance by a conventional method and then added to the organic solvent containing hydrobromic acid. Where the conversion reaction is carried out without previous change into free bases, the conversion can be accelerated by increasing the amount of hydrobromic acid or elevating the heating temperature when the conversion rate is slow.

In this case, the same organic solvents as mentioned hereinbefore are all usable. The organic solvent is preferably used in an amount of about 1–3 liters, most preferably about 2 liters, per mole of the total amount of the starting E-isomer and Z-isomer of the triphenylethylene compound of the formula (I) or the salts thereof.

As described above, it is preferable to use hydrobromic acid having a concentration of at least about 30 wt. %. The hydrobromic acid is preferably used in an amount of 0.05 to 1.5 moles, calculated as hydrogen bromide, per mole of the starting mixture (i.e., per mole of the total amount of the. E-isomer or its acid addition salt and the Z-isomer or its acid addition salt). When the E-isomer and Z-isomer are used in the form of free bases, hydrobromic acid is preferably used in an amount slightly exceeding the equimolar amount, particularly about 1.1–1.5 moles, most preferably about 1.2 moles, calculated as hydrogen bromide, per mole of the total amount of the E-isomer free base and the Z-isomer free base. When the E-isomer and Z-isomer are used in the form of acid addition salts, a small amount of hydrobromic acid is sufficient, and it is generally preferable that hydrobromic acid is used in an amount of 0.05 to 0.5 mole, most suitably 0.2 mole, calculated as hydrogen bromide, per mole of the total amount of the acid addition salts of the E- and Z-isomers.

Either when the E-isomer of the compound of the formula (I) or its acid addition salt is used singly as the starting material or when the same is used in admixture with the Z-isomer or its acid addition salt, heating for the conversion is continued until most of the acid addition salt of the E-isomer in the organic solvent is converted to the Z-isomer and crystallized. The heating temperature is generally in the range of 30° C. to the boiling point of the solvent, preferably about 40°–60° C. The heating time is generally 0.5–12 hours, preferably 1–4 hours. Generally, prior to the above heating, it is preferable to heat a system containing the starting material, the organic solvent and hydrogen bromide under reduced pressure (generally about 40–60 mmHg) at a vapor temperature of 30°–40° C., thereby evaporating water in the system together with the organic solvent, to add the above-mentioned amount of the organic solvent again to the resulting residue or concentrate, and then to carry out the above heating. These steps, however, are not always necessary.

The progress of the conversion can be monitored by high performance liquid chromatography (HPLC) or nuclear magnetic resonance spectroscopy. By cooling the reaction mixture to room temperature or about 0° C. after the completion of the heating step, the desired Z-isomer is precipitated as a hydrobromic acid salt or other acid addition salt from the reaction mixture, whereas most of the unreacted E-isomer acid addition salt remains as dissolved in the solution. The crystals obtained from this slurry by a known separation method such as filtration or centrifugation are of sufficiently high purity as the Z-isomer acid addition salt. The purity can be further improved, for example, by washing the crystals with an organic solvent which does not dissolve the crystals.

Among the acid addition salts of the Z-isomer of the compound of the formula (I) thus obtained, those useful as the intermediates can be converted by a known method, such as one described in Japanese Examined Patent Publication (Kokoku) No. 57277/1993, to the Z-isomers of the end products or their acid addition salts useful as antiestrogenic agents.

BEST MODE FOR CARRYING OUT THE INVENTION

Preparation of the Z-isomer acid addition salts according to the present invention is given below as Examples. For comparison, preparation of an acid addition salt of the Z-isomer according to the prior art (Japanese Examined Patent Publication (Kokoku) No. 75224/1992) is given as Comparative Example 1.

EXAMPLE 1

One kg (1.96 moles) of a mixture of hydrobromic acid salt of the E-isomer of 1-(4-hydroxyphenyl)-2-(4-isopropylphenyl)-1-[4-(2-N,N-dimethylamino)ethoxy]phenyl- 1-butene and hydrobromic acid salt of the Z-isomer thereof (weight ratio of E:Z=67:33) was added to a mixture of 2 liters of ethyl acetate and 0.066 kg (0.38 mole) of a 47% hydrobromic acid and mixed. The solvent was distilled off under reduced pressure at a vapor temperature of 30°–35° C. until water was completely removed.

Two liters of ethyl acetate and 2 liters of toluene were added to the resulting oily concentrate and the resulting mixture was stirred with heating at 60° C. for 4 hours. After cooling to room temperature, the crystals precipitated were filtered off. The crystals thus obtained were washed with a solvent mixture of 1 liter of ethyl acetate and 1 liter of toluene and dried, thus giving 0.9 kg (yield: 90%) of hydrobromic acid salt of the Z-isomer. HPLC analysis showed that the product thus obtained was 100% Z-isomer hydrobromic acid salt.

EXAMPLE 2

A 10 g quantity (0.0215 mole) of a mixture of hydrochloric acid salt of the E-isomer of 1-(4-hydroxyphenyl)-2-(4-isopropylphenyl)-1-[4-(2-N,N-dimethylamino)ethoxy]phenyl-1-butene and hydrochloric acid salt of the corresponding Z-isomer (weight ratio of E:Z=80:20) was added to a mixture of 20 ml of dichloromethane and 1.0 g (0.0058 mole) of a 47% hydrobromic acid and mixed. The solvent was distilled off under reduced pressure at a vapor temperature of 30°–35° C. until water was completely removed.

To the residue was added 20 ml of dichloromethane, and the mixture was stirred with heating under reflux for 8 hours. After cooling to room temperature, the crystals precipitated were filtered off. The crystals were first washed with 50 ml of acetone with stirring under reflux for 1 hour and, after cooling to room temperature, filtered off. The crystals were then purified by washing with 10 ml of acetone and drying, giving 9.0 g (yield: 90%) of Z-isomer salt. HPLC analysis showed that the product thus obtained was 100% Z-isomer salt.

COMPARATIVE EXAMPLE 1

A 2.0 g quantity of a mixture of hydrochloric acid salt of the E-isomer of 1-(4-hydroxyphenyl)-2-(4-isopropylphenyl)-1-[4-(2-N,N-dimethylamino)ethoxy]phenyl- 1-butene and hydrochloric acid salt of the corresponding Z-isomer (weight ratio of E:Z=80:20) was added to 20 ml of a 12N hydrochloric acid. After stirring for 1 hour in the form of a suspension, a jelly-like mass was formed. The mass was heated to 55° C. and maintained at this temperature for 19 hours.

HPLC analysis of this jelly-like product obtained at this stage showed that the amount of the mixture of hydrochloric acid salt of the E-isomer of 1-( 4-hydroxyphenyl)-2-(4-isopropylphenyl)-1-[4-(2-N,N-dimethylamino)ethoxy[phenyl-1-butene and hydrochloric acid salt of the Z-isomer thereof was only about 40% of the initial amount, and that about 60% of the initial amount had been decomposed. The ratio by weight of the E-isomer hydrochloric acid to the Z-isomer hydrochloric acid in the remaining mixture was E:Z=73:27.

It was revealed from the above results that if the conversion is carried out by the method described in Japanese Examined Patent Publication (Kokoku) No. 75224/1992, the hydrochloric acid salt of the E-isomer of 1-(4-hydroxyphenyl)-2-(4-isopropylphenyl)-1-[4-(2-N,N-dimethylamino)ethoxy]phenyl-1-butene is hardly converted to the corresponding Z-isomer hydrochloric acid salt but simply decomposed.

INDUSTRIAL APPLICABILITY

According to the present invention, it is now possible to produce the Z-isomer of the triphenylethylene compound from the E-isomer thereof selectively and within a relatively short period of time using a small amount of hydrobromic acid, and to thereby reduce the production costs to a great extent.

We claim:
1. A process for preparing an acid addition salt of the Z-isomer of a triphenylethylene compound of the formula (I)

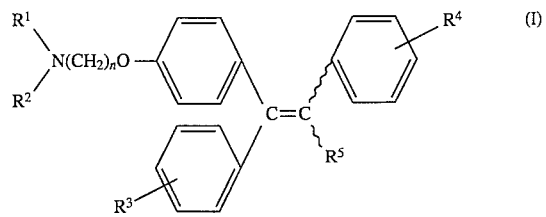

wherein $R^1$ and $R^2$ are the same or different and they each represent a lower alkyl group, or $R^1$ and $R^2$, taken together with the nitrogen atom to which they are attached, may form a nitrogen-containing heterocyclic group which optionally contains other hetero atom or atoms; $R^3$ and $R^4$ are the same or different and they each represent a hydrogen atom, a lower alkyl group, a hydroxyl group, a lower alkoxy group, a lower alkylcarbonyloxy group, an arylcarbonyloxy group optionally substituted with one or two substituents selected from the group consisting of a lower alkyl group, a lower alkoxy group, a halogen atom and a cyano group on the benzene ring, a benzylcarbonyloxy group, a mono- or di(lower alkyl)aminocarbonyloxy group or a mono- or di(aryl)aminocarbonyloxy group; $R^5$ represents a lower alkyl group or a halogen atom; and n represents an integer of 1–6, the process being characterized in that the E-isomer of the triphenylethylene compound of the formula (I) or an acid addition salt thereof is heated in an organic solvent which contains hydrobromic acid.

2. The process according to claim 1 wherein the E-isomer of the compound of the formula (I) or its acid addition salt is heated as admixed with the Z-isomer of the compound of the formula (I) or its acid addition salt.

3. The process according to claim 1 wherein the acid addition salt is a hydrochloric acid salt, a hydrobromic acid salt, a sulfuric acid salt, a phosphoric acid salt, an acetic acid salt, an oxalic acid salt, a maleic acid salt, a fumaric acid salt, a malic acid salt, a tartaric acid salt, a citric acid salt, a benzoic acid salt, a p-toluenesulfonic acid salt or an ethanesulfonic acid salt.

4. The process according to claim 1 wherein the organic solvent is at least one member selected from the group consisting of benzene, toluene, xylene, dichloromethane, chloroform, diethyl ether, tetrahydrofuran, dioxane, anisole, methyl acetate, ethyl acetate, acetone, methyl ethyl ketone, acetonitrile, dimethylsulfoxide, N,N-dimethylformamide and N,N-dimethylacetamide.

5. The process according to claim 1 wherein the acid addition salt is a hydrobromic acid salt or a hydrochloric acid salt.

6. The process according to claim 1 wherein the heating is conducted at a temperature between 30° C. and the boiling point of the organic solvent.

7. The process according to claim 1 wherein the heating is carried out for 0.5–12 hours.

8. The process according to claim 1 wherein hydrobromic acid is used in an amount of 0.05–1.5 moles, calculated as hydrogen bromide, per mole of the E-isomer of the compound of the formula (I) or an acid addition salt thereof.

9. The process according to claim 2 wherein hydrobromic acid is used in an amount of 0.05–1.5 moles, calculated as hydrogen bromide, per mole of the mixture of the E-isomer of the compound of the formula (I) or its acid addition salt and the Z-isomer of the compound of the formula (I) or its acid addition salt.

10. The process according to claim 1 wherein the organic solvent is used in an amount of 1–3 liters per mole of the E-isomer of the compound of the formula (I) or its acid addition salt.

11. The process according to claim 2 wherein the organic solvent is used in an amount of 1–3 liters per mole of the total amount of the E-isomer of the compound of the formula (I) or its acid addition salt and the Z-isomer of the compound of the formula (I) or its acid addition salt.

12. The process according to claim 1 which comprises mixing the E-isomer of the compound of the formula (I) or its acid addition salt, the organic solvent and the hydrobromic acid, distilling the mixture under reduced pressure until water is removed, adding the organic solvent to the thus-obtained residue or concentrate and heating the resulting reaction system.

13. The process according to claim 2 which comprises mixing the E-isomer of the compound of the formula (I) or its acid addition salt, the Z-isomer of the compound of the formula (I) or its acid addition salt, the organic solvent and the hydrobromic acid, distilling the mixture under reduced pressure until water is removed, adding the organic solvent to the thus-obtained residue or concentrate and heating the resulting reaction system.

14. The process according to claim 1 wherein $R^1$ and $R^2$ are the same or different and each represents a lower alkyl group, $R^3$ and $R^4$ are the same or different and each represents a hydrogen atom, a lower alkyl group or a hydroxyl group, and $R^5$ represents a lower alkyl group.

15. The process according to claim 1 wherein $R^1$ and $R^2$ represent methyl group, $R^3$ represents 4-hydroxyl group, $R^4$ represents 4-isopropyl group, $R^5$ represents ethyl group and n is 2.

* * * * *

UNITED STATES PATENT AND TRADEMARK OFFICE
CERTIFICATE OF CORRECTION

PATENT NO. : 5,565,611
DATED : October 15, 1996
INVENTOR(S) : Fumihiko et al

It is certified that error appears in the above-indentified patent and that said Letters Patent is hereby corrected as shown below:

On the title page:

Item [75], lines [1-3], please delete all inventors' names, insert therefor:

first inventor -- Fumihiko Shinozaki -- second inventor -- Hiroshi Nagasawa -- third inventor -- Maruhashi Kazuo --

Signed and Sealed this

Seventh Day of January, 1997

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,565,611
DATED : October 15, 1996
INVENTOR(S) : Shinozaki, et al It is certified that error appears in the above-identified patent and that said Letters Patent is hereby corrected as shown below:

On the title page, item [22], should read -- [22] PCT Filed: Oct. 25, 1994--.

The PCT data was omitted, insert therefor

Item [86] PCT No.:        PCT/JP94/01782

§ 371 Date:     June 6, 1995

§ 102(e) Date:  June 6, 1995

Item [87] PCT Pub. No.:   WO 95/11879

PCT Pub. Date:  May 4, 1995

Signed and Sealed this

First Day of April, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,565,611
DATED : October 15, 1996
INVENTOR(S) : FUMIHIKO et al.

It is certified that error appears in the above-identified patent and that said Letters Patent is hereby corrected as shown below:

TITLE PAGE:
Item [56], FOREIGN PATENT DOCUMENTS, line 2, delete "Japan"

insert therefor -- European Patent Office --.

Signed and Sealed this

Ninth Day of June, 1998

BRUCE LEHMAN

Attest:

Attesting Officer

Commissioner of Patents and Trademarks